(12) United States Patent
Chi et al.

(10) Patent No.: US 8,580,961 B2
(45) Date of Patent: Nov. 12, 2013

(54) 2-PHENYL-6-AZOLYLPYRIDINE-BASED LIGAND AND GROUP VIII TRANSITION METAL COMPLEX

(75) Inventors: Yun Chi, Hsinchu (TW); Chien-Wei Hsu, Hsinchu (TW); Shu-Te Ho, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 13/618,210

(22) Filed: Sep. 14, 2012

(65) Prior Publication Data

US 2013/0018189 A1 Jan. 17, 2013

Related U.S. Application Data (63) Continuation-in-part of application No. 12/966,405, filed on Dec. 13, 2010, now Pat. No. 8,507,679.

(30) Foreign Application Priority Data

Jan. 9, 2012 (TW) .............................. 101100791 A (51) Int. Cl.
*C07F 15/00* (2006.01)
*C07D 401/04* (2006.01)
(52) U.S. Cl.
USPC .......................... 546/2; 546/272.4; 546/275.4
(58) Field of Classification Search
USPC ........................ 546/2, 272.4, 275.4
See application file for complete search history.

(56) References Cited

U.S. PATENT DOCUMENTS

2011/0277841 A1  11/2011  Chi et al.

FOREIGN PATENT DOCUMENTS

JP     2008-303152 A   * 12/2008   .............. H01L 51/50

* cited by examiner

*Primary Examiner* — Charanjit Aulakh
(74) *Attorney, Agent, or Firm* — Birch, Stewart, Kolasch & Birch, LLP (57) ABSTRACT

A 2-phenyl-6-azolylpyridine-based ligand is represented by the following formula (I):

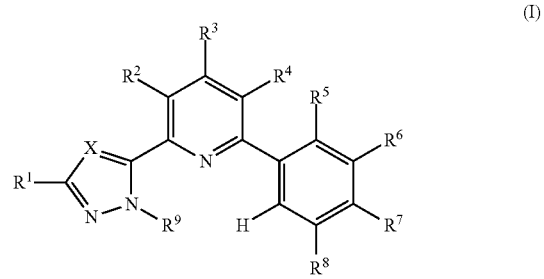

(I)

wherein, X represents nitrogen or C—$R^{10}$; $R^1$, $R^2$, $R^3$, $R^4$, $R^5$, $R^6$, $R^7$, $R^8$ and $R^{10}$ independently represent hydrogen, halogen, a cyano group, an amino group, an optionally substituted aryl group, an optionally substituted heteroaryl group, sulfate, —COOH, an alkoxy group, a carbonyl group, a $C_1$-$C_{10}$ haloalkyl group, a $C_1$-$C_{12}$ alkyl group, a $C_2$-$C_{10}$ alkenyl group, a $C_2$-$C_{10}$ alkynyl group, a $C_3$-$C_{20}$ cycloalkyl group, a $C_3$-$C_{20}$ cycloalkenyl group, a $C_1$-$C_{20}$ heterocycloalkyl group, or a $C_1$-$C_{20}$ heterocycloalkenyl group; and $R^9$ represents hydrogen or alkali metal.

16 Claims, 2 Drawing Sheets

2-PHENYL-6-AZOLYLPYRIDINE-BASED LIGAND AND GROUP VIII TRANSITION METAL COMPLEX

CROSS-REFERENCE TO RELATED APPLICATION

This application claims priority of Taiwanese application no. 101100791, filed on Jan. 9, 2012. This application is also a continuation-in-part (CIP) of U.S. patent application Ser. No. 12/966,405, filed on Dec. 13, 2010, now U.S. Pat. No. 8,507,679 the entire disclosure of which is incorporated herein by reference.

BACKGROUND OF THE INVENTION

1. Field of the Invention

This invention relates to a pyridine-based compound and a metal complex containing the pyridine-based compound, and particularly to a 2-phenyl-6-azolylpyridine-based ligand and a Group VIII transition metal complex containing the 2-phenyl-6-azolylpyridine-based ligand.

2. Description of the Related Art

In recent years, solar cells have been developed with the increasing demand for energy. In particular, the dye-sensitized solar cells have been most promise among solar cells. The dye-sensitized solar cells absorb visible light and near infrared light to excite electrons. The excited electrons are effectively transferred to a conduction band of a semiconductor in the dye-sensitized solar cells to generate a photocurrent. Therefore, the property of a dye used in the dye-sensitized solar cells will affect directly the photoelectric conversion efficiency of the dye-sensitized solar cell. At present, the ruthenium complex is the main target of research for the dye in the solar cell.

U.S. Pat. No. 7,790,980 discloses a dye comprising a Group VIII transition metal complex represented by the following formula (1):

wherein, $M^1$ represents Group VIII transition metal complex; each of $T^1$ and $T^2$ is independently selected from ligands represented by the following formula (1a):

In formula (1a), n is either 0 or 1, each of $r^1$, $r^2$ and $r^3$ is independently selected from the group consisting of: —COOH, —PO$_3$H, —SO$_3$H, —CO$_2^-$, —PO$_3^-$, —SO$_3^-$, a $C_1$-$C_{20}$ substituted alkyl group, a $C_1$-$C_{20}$ unsubstituted alkyl groups, a $C_6$-$C_{30}$ substituted aryl group, a $C_6$-$C_{30}$ unsubstituted aryl group, a $C_6$-$C_{30}$ substituted aryloxy group, a $C_6$-$C_{30}$ unsubstituted aryloxy group, a $C_6$-$C_{30}$ substituted arylene group, a $C_6$-$C_{30}$ unsubstituted arylene group, a $C_1$-$C_{20}$ substituted alkylene group, a $C_1$-$C_{20}$ unsubstituted alkylene group, a $C_1$-$C_{20}$ substituted alkyleneoxy group, and a $C_1$-$C_{20}$ unsubstituted alkyleneoxy group;

$G^1$ is selected from the group consisting of: hydrogen, NO$_2$, Cl, Br, I, CN, NCS, H$_2$O, NH$_3$, Cl$^-$, Br$^-$, I$^-$, CN$^-$, NCS$^-$, and PF$_6^-$;

$G^2$ is selected from the group consisting of imidazolium cations, pyridinium cations, pyrrolidinium cations, and quinolidinium cations; and each of m1 and m3 is an integer ranging from 0 to 3; m2 is an integer ranging from 1 to 3; and m4 is an integer ranging from 1 to 6.

However, the photoelectric conversion efficiency of the metal complex in U.S. Pat. No. 7,790,980 and the absorption of the same in the visible light region and near infrared light region are insufficient. In addition, in exemplary examples of U.S. Pat. No. 7,790,980, because the metal complex includes two thiocyanate (NCS) ligands having weaker ligand bonding strength, chelation of the ligands with ruthenium is weak and unstable, thereby resulting in poor photoelectric conversion efficiency and short lifespan of the dye-sensitized solar cell.

SUMMARY OF THE INVENTION

Therefore, the object of the present invention is to provide a novel pyridine-based compound having a wider light absorption region and a transition metal complex containing the pyridine-based compound, so that the dye-sensitized solar cell that contains the transition metal complex can exhibit an improved photoelectric conversion efficiency and longer lifespan.

According to one aspect of the present invention, there is provided a 2-phenyl-6-azolylpyridine-based ligand represented by the following formula (I):

wherein, X represents nitrogen or C—$R^{10}$; $R^1$, $R^2$, $R^3$, $R^4$, $R^5$, $R^6$, $R^7$, $R^8$ and $R^{10}$ independently represent hydrogen, halogen, a cyano group, an amino group, an optionally substituted aryl group, an optionally substituted heteroaryl group, sulfate, —COOH, an alkoxy group, a carbonyl group, a $C_1$-$C_{10}$ haloalkyl group, a $C_1$-$C_{12}$ alkyl group, a $C_2$-$C_{10}$ alkenyl group, a $C_2$-$C_{10}$ alkynyl group, a $C_3$-$C_{20}$ cycloalkyl group, a $C_3$-$C_{20}$ cycloalkenyl group, a $C_1$-$C_{20}$ heterocycloalkyl group, or a $C_1$-$C_{20}$ heterocycloalkenyl group; and $R^9$ represents hydrogen or alkali metal.

According to another aspect of the present invention, there is provided a transition metal complex represented by the following formula (II):

wherein M is a transition metal, $L^1$ being the aforesaid 2-phenyl-6-azolylpyridine-based ligand, $L^2$ being a carboxybipyridine-based ligand.

BRIEF DESCRIPTION OF THE DRAWINGS

Other features and advantages of the present invention will become apparent in the following detailed description of the preferred embodiments of this invention, with reference to the accompanying drawings, in which.

DETAILED DESCRIPTION OF THE PREFERRED EMBODIMENTS

This invention provides a 2-phenyl-6-azolylpyridine-based ligand represented by the following formula (I):

(I)

wherein, X represents nitrogen or C—$R^{10}$; $R^1$, $R^2$, $R^3$, $R^4$, $R^5$, $R^6$, $R^7$, $R^8$ and $R^{10}$ independently represent hydrogen, halogen, a cyano group, an amino group, an optionally substituted aryl group, an optionally substituted heteroaryl group, sulfate, —COOH, an alkoxy group, a carbonyl group, a $C_1$-$C_{10}$ haloalkyl group, a $C_1$-$C_{12}$ alkyl group, a $C_2$-$C_{10}$ alkenyl group, a $C_2$-$C_{10}$ alkynyl group, a $C_3$-$C_{20}$ cycloalkyl group, a $C_3$-$C_{20}$ cycloalkenyl group, a $C_1$-$C_{20}$ heterocycloalkyl group, or a $C_1$-$C_{20}$ heterocycloalkenyl group; and $R^9$ represents hydrogen or alkali metal.

In $R^1$, $R^2$, $R^3$, $R^4$, $R^5$, $R^6$, $R^7$, $R^8$ and $R^{10}$, the optionally substituted aryl group is and the optionally substituted heteroaryl group is selected from the group consisting of $R^{11}$, $R^{12}$, $R^{13}$, $R^{14}$, $R^{15}$, $R^{16}$, $R^{19}$, $R^{20}$, $R^{21}$, and $R^{22}$ independently represent hydrogen, halogen, a cyano group, an amino group, a aryl group, a heteroaryl group, an alkoxy group, a $C_1$-$C_{10}$ haloalkyl group, a $C_1$-$C_{12}$ alkyl group, a $C_2$-$C_{10}$ alkenyl group, a $C_2$-$C_{10}$ alkynyl group, a $C_3$-$C_{20}$ cycloalkyl group, a $C_3$-$C_{20}$ cycloalkenyl group, a $C_1$-$C_{20}$ heterocycloalkyl group, or a $C_1$-$C_{20}$ heterocycloalkenyl group.

In $R^1$, $R^2$, $R^3$, $R^4$, $R^5$, $R^6$, $R^7$, $R^8$ and $R^{10}$, the amino group is represented by —$NR^{17}R^{18}$. $R^{17}$ and $R^{18}$ independently represent hydrogen, halogen, a cyano group, an amino group, an aryl group, a heteroaryl group, an alkoxy group, a $C_1$-$C_{10}$ haloalkyl group, a $C_1$-$C_{12}$ alkyl group, a $C_2$-$C_{10}$ alkenyl group, a $C_2$-$C_{10}$ alkynyl group, a $C_3$-$C_{20}$ cycloalkyl group, a $C_3$-$C_{20}$ cycloalkenyl group, a $C_1$-$C_{20}$ heterocycloalkyl group, or a $C_1$-$C_{20}$ heterocycloalkenyl group. Preferably, the amino group is In $R^1$, $R^2$, $R^3$, $R^4$, $R^5$, $R^6$, $R^7$, $R^8$ and $R^{10}$, the alkoxy group includes, but is not limited to, —$OR^{23}$, $R^{23}$ represents aryl, heteroaryl, $C_1$-$C_{10}$ haloalkyl, $C_1$-$C_{12}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, or $C_1$-$C_{20}$ heterocycloalkenyl.

Preferably, X is $CF_3$.
Preferably, one of $R^5$ $R^6$, $R^7$, and $R^8$ is F or $CF_3$.
Preferably, $R^1$ is $CF_3$ and one of $R^5$ $R^6$, $R^7$, and $R^8$ is F or $CF_3$.

Preferably, $R^3$ represents hydrogen, an aryl group, a heteroaryl group, an amino group, a $C_1$-$C_{12}$ alkoxy group, or wherein $R^{24}$ represents hydrogen, halogen, a cyano group, an amino group, an aryl group, a heteroaryl group, an alkoxy group, a $C_1$-$C_{10}$ haloalkyl group, a $C_1$-$C_{12}$ alkyl group, a $C_2$-$C_{10}$ alkenyl group, a $C_2$-$C_{10}$ alkynyl group, a $C_3$-$C_{20}$ cycloalkyl group, a $C_3$-$C_{20}$ cycloalkenyl group, a $C_1$-$C_{20}$ heterocycloalkyl group, or a $C_1$-$C_{20}$ heterocycloalkenyl group.

Examples of the 2-phenyl-6-azolylpyridine-based ligand include, but are not limited to The ligand of the present invention is asymmetrical in structure and this asymmetrical structure enables the absorption peaks of the metal-to-ligand charge transfer effect to be non-overlapping, thereby widening the absorption region of a transition metal complex containing the ligand of the present invention. In addition, since the carbon atoms of the benzene ring can form carbon anions, the carbon anions and the benzene ring have higher electron density than that of the nitrogen anions in the conventional nitrogen-containing ligand, thereby increasing the electron density of a central transition metal. Therefore, the energy level of the transition metal $T_{2g}$ can be effectively raised, thereby reducing the energy level difference between the highest occupied molecular orbital (HOMO) and the lowest occupied molecular orbital (LOMO), and thereby resulting in a red shift of the absorption. Further, by virtue of the design of the groups on the benzene ring, the energy level of the highest occupied molecular orbital of the transition metal complex can be adjusted so that the energy level difference between the highest occupied molecular orbital and the lowest occupied molecular orbital can be freely adjusted as desired. Therefore, the transition metal complex can have an improved absorption with respect to the visible light region and the near infrared light region.

In addition, the energy level difference between the highest occupied molecular orbital and the lowest occupied molecular orbital can be adjusted not only through the number of the nitrogen on the azolyl group of the 2-phenyl-6-azolylpyridine-based ligand, but also through the redox potential of an electrolyte component in the dye-sensitized solar cell. Generally, the energy level potential of the highest occupied molecular orbital (relative to normal hydrogen electrode (NHE) potential) must be greater than the redox potential of the electrolyte component. Based on experience, the energy level difference of the energy level potential of the highest occupied molecular orbital and the redox potential of the electrolyte component is above at least 0.55V such that the complex may have better regeneration efficiency. For example, when the redox potential of the electrolyte component is 0.35V (relative to NHE), the energy level potential of the highest occupied molecular orbital must be at least greater than 0.9V (relative to NHE). In examples of the present invention, the energy level potential of the highest occupied molecular orbital of the Group VIII transition metal complex is 0.92V and 0.96V.

The proper reactants and reaction conditions for the 2-phenyl-6-azolylpyridine-based ligand may be selected based on the substituted groups of the 2-phenyl-6-azolylpyridine-based ligand. It should be noted that, in the chemical formula of the ligand of this invention and the chemical formulas of the reactants used to prepare the ligand of this invention, the same serial number has the same definition. For example, $R^5$ of a first reactant (see below) has the same definition as $R^5$ in formula (I) of this invention.

Preferably, the reaction steps for preparing a 2-phenyl-6-azolylpyridine-based ligand in which X is C—$R^{10}$ comprise: (1) reacting a first reactant and a second reactant in an alkaline condition in the presence of a catalyst under heating to form a first intermediate; (2) reacting the first intermediate and ethyl trifluoroacetate in the presence of an alkaline sodium salt under heating to form a second intermediate; and (3) reacting the second intermediate and a hydrazine compound to obtain the 2-phenyl-6-azolylpyridine-based ligand of the present invention, in which X is C—$R^{10}$.

Preferably, the reaction steps for preparing a 2-phenyl-6-azolylpyridine-based ligand in which X is nitrogen comprise: (1) reacting a first reactant and a second reactant in an alkaline condition in the presence of a catalyst under heating to form a first intermediate; (2) reacting the first intermediate and ammonium chloride in the presence of an alkaline sodium salt under heating to form a second intermediate; and (3) reacting the second intermediate, ethyl trifluoroacetate and a hydrazine compound to obtain the 2-phenyl-6-azolylpyridine-based ligand of the present invention, in which X is nitrogen.

The first reactant is or

The second reactant is wherein L
represents —CN,

Preferably, the alkaline sodium salt includes, but is not limited to, sodium methylate or sodium ethylate.

Preferably, the catalyst is tetrakis(triphenylphosphine)palladium, cuprous iodide, bis(triphenylphosphine)palladium (II) dichloride ($PdCl_2(PPh_3)_2$), bis(tri-tert-butylphosphine)palladium, or combinations thereof. More preferably, the catalyst is tetrakis(triphenylphosphine)palladium.

This invention also provides a transition metal complex represented by the following formula (II):

$$ML^1L^2 \quad (II)$$

wherein M is a transition metal, $L^1$ is the 2-phenyl-6-azolylpyridine-based ligand described above, and $L^2$ is a carboxy-bipyridine-based ligand.

Preferably, M is a Group VIII transition metal. More preferably, M is ruthenium.

Preferably, the carboxy-bipyridine-based ligand is represented by the following formula (III):

(III)

wherein $X^1$, $X^2$, $X^3$, $X^4$, $X^5$, $X^6$ and $X^7$ independently represent hydrogen, halogen, $CF_3$, a $C_1$-$C_{12}$ linear alkyl group, a $C_1$-$C_{12}$ branched alkyl group, a phosphoryl group, a phosphate group, a boric acid group, a borate group, a sulfo group, a sulfonate group, or —COOY, Y being hydrogen, alkali metal, a $C_1$-$C_{12}$ linear alkyl group, a $C_1$-$C_{12}$ branched alkyl group or $N(C_4H_9)_4^+$; with the proviso that at least one of $X^1$, $X^2$, $X^3$, $X^4$, $X^5$, $X^6$ and $X^7$ is —COOY,

$X^8$ is $X^9$, $X^{10}$, $X^{11}$ and $X^{12}$ independently represent hydrogen, halogen, $CF_3$, a carboxylic group, a $C_1$-$C_8$ linear alkyl group, a $C_1$-$C_8$ branched alkyl group, $X^{13}$ and $X^{14}$ independently represent hydrogen, halogen, $CF_3$, a carboxylic group, a $C_1$-$C_8$ linear alkyl group, a $C_1$-$C_8$ branched alkyl group, or $X^{15}$ and $X^{16}$ independently represent a $C_1$-$C_8$ linear alkyl group, a $C_1$-$C_8$ branched alkyl group, an alkoxy group, or an alkylthio group.

Preferably, at least two of $X^1$, $X^2$, $X^3$, $X^4$, $X^5$, $X^6$ and $X^7$ are —COOY.

Preferably, at least two of $X^1$, $X^2$, $X^3$, $X^4$, $X^5$, $X^6$ and X are —COOH.

Preferably, $X^8$ is

Examples of the carboxy-bipyridine-based ligand include, but are not limited to, In accordance with the present invention, based on the design of the 2-phenyl-6-azolylpyridine-based ligand, the energy level difference between the highest occupied molecular orbital and the lowest occupied molecular orbital of the transition metal complex can be freely adjusted so that the transition metal complex can have better absorption in the near infrared light region. It is noted that, as compared to N, O, S or halogen, although the carbon on the benzene ring is deemed difficult to bond to a metal, the transition metal complex of the present invention is proven to have better absorption in the visible light region and the near infrared light region even though the 2-phenyl-6-azolylpyridine-based ligand has the benzene ring.

The reactants and reaction conditions for the transition metal complex may be selected based on the respective substituted groups. There action steps comprise: mixing the abovementioned 2-phenyl-6-azolylpyridine-based ligand and a transition metal source to form a mixture, and heating the mixture in the presence of a catalyst to obtain the Group VIII transition metal complex of the present invention. The metal source is made from a carboxy-bipyridine-based compound and a transition metal. Preferably, the metal source is (4,4',4"-ethoxycarbonyl-terpyridine)$RuCl_3$ (4,4',4"-methoxycarbonyl-terpyridine)$RuCl_3$, (4,4',4"-ethoxycarbonyl-terpyridine)$OsCl_3$, or (4,4',4"-methoxycarbonyl-terpyridine)$OsCl_3$. Preferably, the catalyst is potassium acetate or sodium acetate. After the Group VIII transition metal complex is made, the ester acid functional groups may be hydrolyzed into $CO_2^-$ or COOH through the catalysis of an alkaline reagent. Preferably, the alkaline reagent is a sodium hydroxide (NaOH) solution or a tetrabutyl ammonium hydroxide (TBAOH) solution.

This invention also provides a dye-sensitized solar cell including:

an electrolytic component;

a first electrode disposed in the electrolytic component and including a transparent conductive substrate and a porous film disposed on a surface of the transparent conductive substrate, the porous film absorbing the abovementioned Group VIII transition metal complex; and a second electrode spaced apart from the first electrode and disposed in the electrolytic component.

Examples of the electrolytic component include, but are not limited to, a mixture solution containing 1,3-dimethylimidazolium iodide (DMII, 2M), guanidinium thiocyanate (0.1M), lithium iodide (LiI, 0.05M), iodine ($I_2$, 0.03M), tertbutyl pyridine (0.5M) in a solvent containing acetonitrile and valeronitrile (volume ratio of acetonitrile to valeronitrile is 85:15), tetrabutylammonium hexafluorophosphate ($TBAPF_6$, 0.1M), and a mixture solution containing 1,3-dimethylimidazolium iodide (2M), lithium iodide (0.05M), iodine (0.03M), guanidinium thiocyanate (0.1M), and N-butyl-1H-benzimidazole (NBB, 0.5M) in 3-methyoxy propanenitrile.

Preferably, the electrolytic component is the mixture solution containing 1,3-dimethylimidazolium iodide (DMII, 2M), guanidinium thiocyanate (0.1M), lithium iodide (LiI, 0.05M), iodine ($I_2$, 0.03M), tertbutyl pyridine (0.5M) in a solvent containing acetonitrile and valeronitrile (volume ratio of acetonitrile to valeronitrile is 85:15).

Preferably, the porous film is made of a material selected from titanium dioxide ($TiO_2$), zinc oxide and tin oxide. Preferably, the transparent conductive substrate is made of a flexible polymer material or a rigid material. The flexible polymer material includes, but is not limited to, polyethylene, polypropylene, polyimide, polymethyl methacrylate, polycarbonate, polyethyleneterephthalate, etc. The rigid material includes, but is not limited to, glass.

The method for manufacturing the dye-sensitized solar cell is well known in the art and will not be described in detail hereinafter.

It is noted that, in the conventional transition metal complex, the NCS group is difficult to chelate stably with the transition metal due to weak stability of the single ligand bonding of NCS, and thus is liable to decompose, thereby resulting in poor photoelectric conversion efficiency and lifespan of a dye-sensitized solar cell containing the conventional transition metal complex. On the contrary, since the transition metal complex of the present invention has better absorption in the visible light region and near infrared light region and high molar extinction coefficient because of absence of the NCS, as compared to the conventional dye-sensitized solar cell, the dye-sensitized solar cell containing the transition metal complex of the present invention has increased photoelectric conversion efficiency and lifespan of the dye-sensitized solar cell.

EXAMPLES

[Preparation 1]

1-bromo-3-(trifluoromethyl)benzene (5.00 g, 22 mmol) was placed in a 250 ml reaction flask, followed by injecting and evacuating nitrogen gas three times. Next, dehydrated tetrahydrofuran (THF, 100 ml) was added into the reaction flask, followed by slowly adding 9.8 ml n-butyllithium in hexane solution (2.5M, 24 mmol) at −78° C. and stirring at the same temperature for 30 minutes. Thereafter, 2-isopropoxy-4,4,5,5-tetramethyl-1,3,2-dioxaborolane (5.0 ml, 24 mmol) was added into the reaction flask to obtain a mixture, and the temperature of the mixture was raised to room temperature, followed by stirring at room temperature for 12 hours. Next, water was added to terminate the reaction followed by removing THF using a rotary evaporator. Then, dichloromethane and water were added into the mixture for extraction. The dichloromethane layer was collected and added with magnesium sulfate to remove water therein. After water was removed, the dichloromethane layer was filtrated and the filtrate was collected. Next, the dichloromethane layer was concentrated by means of reduced pressure distillation to obtain a colorless oily liquid (5.21 g, 19 mmol, 86% yield).

The spectrum analysis for the colorless oily liquid is: $^1$H NMR (400 MHz, CDCl$_3$, 298K), δ(ppm): 8.04 (s, 1H), 7.95 (d, $J_{HH}$=7.6 Hz, 1H), 7.68 (d, $J_{HH}$=7.6 Hz, 1H), 7.46 (t, $J_{HH}$=7.6 Hz, 1H), 1.34 (s, 12H). The chemical structure of the colorless oily liquid is

[Preparation 2]

4-bromo-1-fluoro-2-(trifluoromethyl)benzene (2.00 g, 8.2 mmol) was placed in a 250 ml reaction flask, followed by injecting and evacuating nitrogen gas three times. Next, dehydrated THF (50 ml) was added into the reaction flask, followed by slowly adding 3.62 ml n-butyllithium in hexane solution (9.1 mmol) (2.5M, 9.1 mmol) at −78° C. and stirring at the same temperature for 30 minutes. Thereafter, 2-isopropoxy-4,4,5,5-tetramethyl-1,3,2-dioxaborolane (1.85 ml, 9.1 mmol) was added into the reaction flask to obtain a mixture, and the temperature of the mixture was raised to room temperature, followed by stirring at room temperature for 12 hours. Next, water was added to terminate the reaction followed by removing THF using a rotary evaporator. Then, dichloromethane and water were added into the mixture for extraction. The dichloromethane layer was collected and added with magnesium sulfate to remove water therein. After water was removed, the dichloromethane layer was filtrated and the filtrate was collected. Next, the dichloromethane layer was concentrated by means of reduced pressure distillation to obtain a colorless oily liquid (1.95 g, 6.7 mmol, 82% yield).

The spectrum analysis for the colorless oily liquid is: $^1$H NMR (400 MHz, CDCl$_3$, 298K), δ(ppm): 8.03 (d, $J_{HF}$=7.6 Hz, 1H), 7.98~7.90 (m, 1H), 7.16 (t, $J_{HH}$=9.2 Hz, 1H), 1.35 (s, 12H). The chemical structure of the colorless oily liquid is Preparation of 2-phenyl-6-azolylpyridine-Based Ligands

Synthesis Example 1

The colorless oily liquid of Preparation 1 (0.68 g, 2.5 mmol), 6-acetyl-2-bromopyridine (0.50 g, 2.5 mmol) and tetrakis(triphenylphosphine)palladium (Pd(PPh$_3$)$_4$, 144 mg, 0.13 mmol) were added in a 100 ml single neck bottle followed by adding THF (25 ml) and a potassium carbonate solution (potassium carbonate (0.69 g) in deionized water (5 ml)) to obtain a mixture. The mixture was heated under reflux for 16 hours under a nitrogen gas atmosphere. After the reaction was finished, the mixture was cooled to room temperature, followed by removing solvent by virtue of reduced pressure distillation to obtain a distilled mixture. Then, the distilled mixture was added with dichloromethane and water for extraction. The dichloromethane layer was collected and added with magnesium sulfate to remove water. The dichloromethane layer was then filtrated and the filtrate was collected. Next, the filtrate was concentrated by means of reduced pressure distillation to obtain a yellow crude product. The resultant yellow crude product was subjected to column chromatography, in which a mixture of ethyl acetate and hexane (ethyl acetate: hexane=1:8) was used as an eluent. An eluate was collected followed by removing the eluent using a rotary evaporator. A white solid product was obtained (446 mg, 1.7 mmol, 67% yield).

The spectrum analysis for the white solid product is: $^1$H NMR (400 MHz, CDCl$_3$, 298K), δ(ppm): 8.34 (s, 1H), 8.27 (d, $J_{HH}$=8.0 Hz, 1H), 8.02 (dd, $J_{HH}$=6.8 Hz, 2.0 Hz, 1H), 7.98~7.90 (m, 2H), 7.70 (d, $J_{HH}$=8.0 Hz, 1H), 7.63 (t, $J_{HH}$=8.0 Hz, 1H), 2.82 (s, 3H). The chemical structure of the white solid product is

Sodium ethylate (116 mg, 1.7 mmol) and dehydrated THF (20 ml) were added into a 50 ml two-neck bottle in sequence, followed by slowly adding the resultant white solid product (300 ml, 1.1 mmol) at 0° C. and stirring for 20 minutes to obtain a mixture. Thereafter, the temperature of the mixture was raised to room temperature followed by adding ethyl trifluoroacetate (0.20 ml, 1.7 mmol) to obtain a reaction mixture. The reaction mixture was heated to 80° C. and stirred for 4 hours for reaction. After the reaction was finished, hydrogen chloride (2N) was dropwise added into the reaction mixture to adjust pH of the reaction mixture to about 4 and the solvent in the reaction mixture was removed by means of reduced pressure distillation to obtain a distilled mixture. Then, the distilled mixture was added with ethyl acetate and water for extraction. The ethyl acetate layer was collected and added with magnesium sulfate to remove water. The ethyl acetate layer was then filtrated and the filtrate was collected. Next, the filtrate was concentrated by means of reduced pressure distillation to obtain a yellow solid product. The chemical structure of the yellow solid product is The resultant yellow solid product, ethanol (30 ml) and hydrazine (0.33 ml, 6.4 mmol) were added in a 100 ml round bottom flask, followed by heating under reflux for 12 hours. After the reaction was finished, the solvent was removed by means of reduced pressure distillation, followed by conducting column chromatography using a mixture of ethyl acetate and hexane (ethyl acetate: hexane=1:3) as an eluent. Thereafter, recrystallization was conducted to obtain 120 mg (0.34 mmol) colorless transparent crystal (120 mg, 0.34 mmol, 30% yield).

The spectrum analysis for the colorless transparent crystal is: $^1$H NMR (400 MHz, CDCl$_3$, 298K), δ(ppm): 8.25 (s, 1H), 8.20 (d, $J_{HH}$=7.6 Hz, 1H), 7.90 (d, $J_{HH}$=7.6 Hz, 1H), 7.75 (d, $J_{HH}$=7.6 Hz, 1H), 7.71 (d, $J_{HH}$=8.0 Hz, 1H), 7.67~7.58 (m, 2H), 6.99 (s, 1H); MS (EI$^+$): m/z 357 (M)$^-$.

The chemical structure of the colorless transparent crystal is

Synthesis Example 2

2-bromo-6-cyanopyridine (424 mg, 2.3 mmol), 4-(trifluoromethyl)phenylboronic acid (440 mg, 2.3 mmol) and Pd(PPh$_3$)$_4$ (134 mg, 0.12 mmol) were added in a 100 ml single neck bottle, followed by adding THF (30 ml) and a potassium carbonate solution (potassium carbonate (0.96 g) in deionized water (7 ml)) to obtain a mixture. The mixture was heated under reflux for 6 hours under a nitrogen gas atmosphere. After the reaction was finished, the mixture was cooled to room temperature, followed by removing solvent by virtue of reduced pressure distillation to obtain a distilled mixture. Then, the distilled mixture was added with dichloromethane and water for extraction. The dichloromethane layer was collected and added with magnesium sulfate to remove water. The dichloromethane layer was then filtrated and the filtrate was collected. Next, the filtrate was concentrated by means of reduced pressure distillation to obtain a yellow crude product. The resultant yellow crude product was subjected to column chromatography, in which a mixture of ethyl acetate and hexane (ethyl acetate: hexane=1:4) was used as an eluent. An eluate was collected followed by removing the eluent using a rotary evaporator. A white solid product was obtained (460 mg, 1.9 mmol, 80% yield).

The spectrum analysis for the white solid product is: $^1$H NMR (400 MHz, CDCl$_3$, 298K), δ(ppm): 8.14 (d, $J_{HH}$=8.0 Hz, 2H), 8.02~7.90 (m, 2H), 7.75 (d, $J_{HH}$=8.0 Hz, 2H), 7.68 (d, $J_{HH}$=7.2 Hz, 1H). The chemical structure of the white solid product is The resultant white solid product (450 mg, 1.8 mmol) and sodium methylate (9.8 mg, 0.18 mmol) were placed in a 50 ml single neck bottle, followed by adding methanol (15 ml) and stirring at room temperature for 12 hours. Thereafter, ammonium chloride (107 mg, 2.0 mmol) was added into the single neck bottle and the mixture was heated under reflux for 4 hours under a nitrogen gas atmosphere. Subsequently, methanol was removed and ethanol (10 ml) was added into the single neck bottle, followed by heating under reflux for 30 minutes under a nitrogen gas atmosphere. After the reaction was finished and the mixture was cooled to room temperature, evacuation and filtration were conducted so as to obtain a filtrate, followed by collecting and concentrating the filtrate to obtain a yellow solid product (400 mg, 1.3 mmol, 70% yield).

Ethyl trifluoroacetate (0.26 ml, 1.5 mmol) and hydrazine monohydrate (N$_2$H$_4$.H$_2$O, 0.1 ml, 1.9 mmol) were dissolved in THF (25 ml), followed by heating under reflux for 1 hour under a nitrogen gas atmosphere. The mixture was cooled to room temperature, followed by adding the resultant yellow solid product (400 mg, 1.3 mmol) and sodium hydroxide (76 mg, 1.9 mmol) and heating under reflux for 8 hours under a nitrogen gas atmosphere. After the reaction was finished, the solvent was removed by means of reduced pressure distillation to obtain a distilled mixture, followed by neutralization using a saturated sodium hydrocarbonate solution. Next, the distilled mixture was added with ethyl acetate (30 ml) and water for extraction. The ethyl acetate layer was collected and added with magnesium sulfate to remove water. The ethyl acetate layer was then filtrated and the filtrate was collected. Next, the filtrate was concentrated by means of reduced pressure distillation to obtain a yellow crude product. The resultant yellow crude product was subjected to column chromatography, in which a mixture of ethyl acetate and hexane (ethylacetate:hexane=1:2) was used as an eluent, followed by adding ethyl acetate for recrystallization so as to obtain white crystal (190 mg, 0.53 mmol 40% yield).

The spectrum analysis for the white crystal is: $^1$H NMR (400 MHz, CDCl$_3$, 298K), δ(ppm): 12.0 (br, 1H), 8.23 (d, $J_{HH}$=8.0 Hz, 1H), 8.12 (d, $J_{HH}$=8.0 Hz, 2H), 8.01 (t, $J_{HH}$=8.0 Hz, 1H), 7.90 (d, $J_{HH}$=8.0 Hz, 1H), 7.77 (d, $J_{HH}$=8.0 Hz, 2H); MS (EI$^+$): m/z 358 (M)$^+$. The chemical structure of the white crystal is

Synthesis Example 3

2-bromo-6-cyanopyridine (0.50 g, 2.7 mmol), the colorless oily liquid of the preparation 1 (0.89 g, 3.3 mmol) and Pd(PPh$_3$)$_4$ (158 mg, 0.14 mmol) were added into a 100 ml single neck bottle, followed by adding THF (30 ml) and a potassium carbonate solution (potassium carbonate (0.94 g) in deionized water (7 ml)) to obtain a mixture. The mixture was heated under reflux for 4 hours under a nitrogen gas atmosphere. After the reaction was finished, the mixture was cooled to room temperature, followed by solvent removal by virtue of reduced pressure distillation to obtain a distilled mixture. Then, the distilled mixture was added with dichloromethane and water for extraction. The dichloromethane layer was collected and added with magnesium sulfate to remove water. The dichloromethane layer was then filtrated and the filtrate was collected. Next, the filtrate was concentrated by means of reduced pressure distillation to obtain a yellow solid product. The yellow solid product was subjected to column chromatography, in which a mixture of ethyl acetate and hexane (ethyl acetate: hexane=1:4) was used as an eluent. An eluate was collected followed by removing the eluent using a rotary evaporator. A white solid product was obtained (608 mg, 2.4 mmol, 90% yield.

The spectrum analysis for the white solid product is: $^1$H NMR (400 MHz, CDCl$_3$, 298K). δ(ppm): 8.27 (s, 1H), 8.22 (d, J$_{HH}$=8.0 Hz, 1H), 8.02~7.90 (m, 2H), 7.76~7.59 (m, 3H). The chemical structure of the white solid product is The resultant white solid product (600 mg, 2.4 mmol) and sodium methylate (13.1 mg, 0.24 mmol) were added into a 50 ml single neck bottle, followed by adding 15 ml of methanol and stirring at room temperature for 12 hours. Thereafter, ammonium chloride (142 mg, 2.7 mmol) was added into the single neck bottle and the mixture was heated under reflux for 4 hours under a nitrogen gas atmosphere. After the reaction was finished, methanol was removed by means of reduced pressure distillation. Evacuation and filtration were conducted after the mixture was cooled to room temperature so as to obtain a filtrate, followed by concentrating the filtrate to obtain a yellow solid product (700 mg, 2.3 mmol, 96% yield).

Ethyl trifluoroacetate (0.29 ml, 1.5 mmol) and hydrazine monohydrate (N$_2$H$_4$.H$_2$O, 0.12 ml, 2.3 mmol) were dissolved in THF (30 ml), followed by heating under reflux for 1 hour under a nitrogen gas atmosphere. The mixture was cooled to room temperature, followed by adding the yellow solid product (700 mg, 2.3 mmol) and sodium hydroxide (94 mg, 2.3 mmol) and heating under reflux for 8 hours under a nitrogen gas atmosphere. After the reaction was finished, the solvent was removed by means of reduced pressure distillation to obtain a distilled mixture, followed by neutralization using a saturated sodium hydrocarbonate solution. Next, the distilled mixture was added with ethyl acetate (30 ml) and water for extraction. The ethyl acetate layer was collected and added with magnesium sulfate to remove water. The ethyl acetate layer was then filtrated and the filtrate was collected. Next, the filtrate was concentrated by means of reduced pressure distillation, followed by column chromatography using a mixture of ethyl acetate and hexane (ethyl acetate: hexane=1:2) as an eluent. Thereafter, ethyl acetate was added for recrystallization so as to obtain white crystal (220 mg, 0.61 mmol, 26% yield).

The spectrum analysis for the white crystal is: NMR (400 MHz, CDCl$_3$, 298K), δ(ppm): 8.26 (s, 1H), 8.22 (d, J$_{HH}$=7.6 Hz, 1H), 8.18 (d, J$_{HH}$=7.6 Hz, 1H), 8.01 (t, J$_{HH}$=7.6 Hz, 1H), 7.89 (d, J$_{HH}$=7.6 Hz, 1H), 7.73 (d, J$_{HH}$=7.6 Hz, 1H), 7.63 (t, J$_{HH}$=7.6 Hz, 1H); MS (EI$^+$): m/z 358 (M)$^+$. The chemical structure of the white crystal is

Synthesis Example 4

2-bromo-6-cyanopyridine (1.10 g, 6.0 mmol), the colorless oily liquid of Preparation 2 (2 g, 6.9 mmol) and Pd(PPh$_3$)$_4$ (346 mg, 0.30 mmol) were added in a 100 ml single neck bottle, followed by adding THF (30 ml) and a potassium carbonate solution (potassium carbonate (2.07 g) in deionized water (7 ml)) to obtain a mixture. The mixture was heated under reflux for 5 hours under a nitrogen gas atmosphere. After the reaction was finished, the mixture was cooled to room temperature, followed by solvent removal by virtue of reduced pressure distillation to obtain a distilled mixture. Then, the distilled mixture was added with dichloromethane and water for extraction. The dichloromethane layer was collected and added with magnesium sulfate to remove water. Filtration was conducted after water was removed and a filtrate was collected. Next, the filtrate was concentrated by means of reduced pressure distillation to obtain a yellow solid product. The yellow solid product was subjected to column chromatography, in which a mixture of ethyl acetate and hexane (ethyl acetate: hexane=1:4) was used as an eluent. An eluate was collected followed by removing the eluent using a rotary evaporator. A white solid product was obtained (983 mg, 3.7 mmo, 61% yield).

The spectrum analysis for the white solid product is: $^1$H NMR (400 MHz, CDCl$_3$, 298K), δ(ppm): 8.30~8.21 (m, 2H), 7.96~7.91 (m, 2H), 7.70~7.63 (m, 1H), 7.33 (t, J$_{HF}$=9.2 Hz, 1H). The chemical structure of the white solid product is The resultant white solid product (703 mg, 2.6 mmol) and sodium methylate (14.3 mg, 0.26 mmol) were added in a 50 ml single neck bottle, followed by adding 20 ml of methanol and stirring at room temperature for 12 hours. Thereafter, ammonium chloride (155 mg, 2.9 mmol) was added into the single neck bottle and the mixture was heated under reflux for 4 hours under a nitrogen gas atmosphere. Subsequently, methanol was removed by means of reduced pressure distillation. Evacuation and filtration were conducted after the mixture was cooled to room temperature so as to obtain a filtrate, followed by concentrating the filtrate to obtain a yellow solid product (820 mg, 2.6 mmol, 97% yield).

Ethyl trifluoroacetate (0.315 ml, 1.9 mmol) and hydrazine monohydrate ($N_2H_4 \cdot H_2O$, 0.129 ml, 2.5 mmol) were dissolved in THF (30 ml), followed by heating under reflux for 1 hour under a nitrogen gas atmosphere. The mixture was cooled to room temperature, followed by adding the yellow solid product (820 mg, 2.6 mmol) and sodium hydroxide (106 mg, 2.6 mmol) and heating under reflux for 8 hours under a nitrogen gas atmosphere. After the reaction was finished, the solvent was removed by means of reduced pressure distillation to obtain a distilled mixture, followed by neutralization using a saturated sodium hydrocarbonate solution. Next, the distilled mixture was added with ethyl acetate (30 ml) and water for extraction. The ethyl acetate layer was collected and added with magnesium sulfate to remove water. Filtration was conducted after water was removed and a filtrate was collected. Next, the filtrate was concentrated by means of reduced pressure distillation, followed by column chromatography using a mixture of ethyl acetate and hexane (ethyl acetate: hexane=1:3) as an eluent. Thereafter, ethyl acetate was added for recrystallization so as to obtain a white crystal (583 mg, 1.5 mmol, 59% yield).

The spectrum analysis for the white crystal is: $^1$H NMR (400 MHz, CDCl$_3$, 298K), δ(ppm): 12.1 (br, 1H), 8.26 (d, $J_{HF}$=6.8 Hz, 1H), 8.24~8.16 (m, 2H), 8.00 (t, $J_{HH}$=8.0 Hz, 1H), 7.85 (d, $J_{HH}$=8.0 Hz, 1H), 7.35 (t, $J_{HF}$=9.2 Hz, 1H); MS (EI$^+$): m/z 376 (M)$^+$. The chemical structure of the white crystal is Synthesis Example 5

2,4-dichloropyridine (1.61 g, 10.9 mmol), 4-(trifluoromethyl)phenylboronic acid (2.00 g, 10.9 mmol) and Pd(PPh$_3$)$_4$ (0.38 g, 0.33 mmol) were placed in a 100 ml single neck bottle, followed by adding THF (40 ml) and a potassium carbonate solution (potassium carbonate (3.76 g) in deionized water (10 ml)) to obtain a mixture. The mixture was heated under reflux for 9 hours under a nitrogen gas atmosphere. After the reaction was finished, the mixture was cooled to room temperature, followed by solvent removal by virtue of reduced pressure distillation to obtain a distilled mixture. Then, the distilled mixture was added with dichloromethane and water for extraction. The dichloromethane layer was collected and added with magnesium sulfate to remove water. Filtration was conducted after water was removed and a filtrate was collected. Next, the filtrate was concentrated by means of reduced pressure distillation to obtain an orange oily product. The orange oily product was subjected to column chromatography, in which ethyl acetate was used as an eluent. An eluate was collected followed by removing the eluent using a rotary evaporator so as to obtain a white solid product (2.18 g, 8.4 mmol, 78% yield).

The spectrum analysis for the white solid product is: $^1$H NMR (400 MHz, CDCl$_3$, 298K), δ(ppm): 8.60 (d, $J_{HH}$=5.2 Hz, 1H), 8.08 (d, $J_{HH}$=8.0 Hz, 2H), 7.77~7.70 (m, 3H), 7.30 (dd, $J_{HH}$=5.2, 1.6 Hz, 1H). The chemical structure of the white solid product is The resultant white solid product (2.15 g, 8.3 mmol) and acetic acid (10 ml) were placed in a 150 ml single neck bottle, followed by adding hydrogen peroxide (10 ml, 30%) in an ice bath and stirring at 80° C. for 24 hours. After the reaction was finished, the mixture was neutralized to pH=7 using a sodium hydroxide solution, and a large amount of solid was precipitated. The solid was filtrated and washed with water and ether several times, followed by drying under vacuum to obtain a white product (1.83 g, 6.7 mmol, 80% yield).

The resultant white product (1.83 g, 6.7 mmol) was placed in a 100 ml two-neck bottle, followed by injecting and evacuating nitrogen gas three times and adding dehydrated dichloromethane (50 ml). Next, dimethylcarbamyl chloride (0.62 ml, 6.7 mmol) and trimethylsilyl cyanide (0.90 ml, 7.0 mmol) were slowly added into the two-neck bottle to obtain a mixture. The mixture was stirred at room temperature for two days and then was heated under reflux for 9 hours. After the reaction was finished, the mixture was slowly added with a potassium carbonate solution (10%) in an ice bath, following by stirring for 15 minutes. Next, water was added for extraction and an organic layer was collected, followed by removing water from the organic layer using magnesium sulfate. After water was removed, the organic layer was filtrated and a filtrate was collected, followed by removing the solvent by means of reduced pressure distillation to obtain a distilled mixture. Thereafter, the distilled mixture was subjected to column chromatography using a mixture of ethyl acetate and hexane (ethyl acetate: hexane=1:6) as an eluent. An eluate was collected followed by removing the eluent using a rotary evaporator. A white product was obtained (0.71 g, 2.5 mmol, 91% yield).

The spectrum analysis for the white product is: $^1$H NMR (400 MHz, CDCl$_3$, 298K), δ(ppm): 8.12 (d, $J_{HH}$=8.0 Hz, 2H), 7.96 (d, $J_{HH}$=1.6 Hz, 1H), 7.75 (d, $J_{HH}$=8.0 Hz, 2H). 7.67 (d, $J_{HH}$=1.6 Hz, 1H). The chemical structure of the white product is The white product (698 mg, 2.5 mmol) was placed in a 100 ml two-neck bottle, followed by adding 2-(5-hexylthiophen-2-yl)-4,4,5,5-tetramethyl-1,3,2-di oxaborolane (872 mg, 3.0 mmol), Pd(PPh$_3$)$_4$ (143 mg, 0.12 mmol), THF (30 ml), and a potassium carbonate solution (potassium carbonate (683 mg) in deionized water (6 ml)). The mixture was heated under reflux for 8 hours in a nitrogen gas atmosphere. After the reaction was finished, the mixture was cooled to room temperature, followed by removing solvent by virtue of reduced pressure distillation to obtain a distilled mixture. Then, the distilled mixture was added with dichloromethane and water for extraction and the dichloromethane layer was collected, followed by removing water from the dichloromethane layer using magnesium sulfate. Filtration was conducted after water was removed and a filtrate was collected. Next, the filtrate was concentrated by means of reduced pressure distillation to obtain an orange oily product. The orange oily product was subjected to column chromatography using a mixture of ethyl acetate and hexane (ethyl acetate: hexane=1:5) as an eluent. An eluate was collected followed by removing the eluent using a rotary evaporator. A white solid product was obtained (850 mg, 2.1 mmol, 83% yield).

The spectrum analysis for the white solid product is: $^1$H NMR (400 MHz, CDCl$_3$, 298K), δ(ppm): 8.14 (d, J$_{HH}$=8.0 Hz, 2H), 7.98 (d, J$_{HH}$=1.2 Hz, 1H), 7.79~7.73 (m, 3H), 7.45 (d, J$_{HH}$=3.6 Hz, 1H), 6.86 (d, J$_{HH}$=3.6 Hz, 1H), 2.86 (t, J$_{HH}$=7.6 Hz, 2H), 1.71 (q, J$_{HH}$=7.6 Hz, 2H), 1.43~1.25 (m, 6H), 0.88 (t, J$_{HH}$=6.8 Hz, 3H). The chemical structure of the white solid product is The white solid product (620 mg, 1.5 mmol) and sodium methylate (8.1 mg, 0.15 mmol) were placed in a 50 ml single neck bottle, followed by adding methanol (30 ml) and stirring at room temperature for 12 hours. Thereafter, ammonium chloride (88 mg, 1.7 mmol) was added into the single neck bottle and the mixture was heated under reflux for 4 hours under a nitrogen gas atmosphere. Subsequently, methanol was removed by means of reduced pressure distillation. Evacuation and filtration were conducted after the mixture was cooled to room temperature, followed by collecting and concentrating a filtrate to obtain a yellow solid product (609 mg, 1.3 mmol, 87% yield.

Ethyl trifluoroacetate (0.18 ml, 1.1 mmol) and hydrazine monohydrate (0.073 ml, 1.4 mmol) were dissolved in THF (30 ml), followed by heating under reflux for 1 hour under a nitrogen gas atmosphere. The mixture was cooled to room temperature, followed by adding the yellow solid product (609 mg, 1.3 mmol) and sodium hydroxide (60 mg, 1.5 mmol) and heating under reflux for 8 hours under a nitrogen gas atmosphere. After the reaction was finished, the solvent was removed by means of reduced pressure distillation, followed by neutralization using a saturated sodium hydrocarbonate solution. Ethyl acetate (30 ml) and water were added for extraction. The ethyl acetate layer was collected and added with magnesium sulfate to remove water. Filtration was conducted after water was removed and a filtrate was collected. Next, the filtrate was concentrated by means of reduced pressure distillation to obtain a distilled mixture. The distilled mixture was subjected to column chromatography using a mixture of ethyl acetate and hexane (ethyl acetate: hexane=1:5) as an eluent. Thereafter, ethyl acetate was added for recrystallization so as to obtain white crystal (260 mg, 0.05 mmol, 33% yield).

The spectrum analysis for the white crystal is: $^1$H NMR (400 MHz, CDCl$_3$, 298K), δ(ppm): 12.24 (br, 1H), 8.32 (d, J$_{HH}$=1.6 Hz, 1H), 8.13 (d, J$_{HH}$=8.0 Hz, 2H), 7.90 (d, J$_{HH}$=1.6 Hz, 1H), 7.76 (d, J$_{HH}$=8.0 Hz, 2H), 7.53 (d, J$_{HH}$=3.6 Hz, 1H), 6.85 (d, J$_{HH}$=3.6 Hz, 1H), 2.86 (t, J$_{HH}$=7.6 Hz, 2H), 1.71 (q, J$_{HH}$=7.6 Hz, 2H), 1.50~1.25 (m, 6H), 0.90 (t, J$_{HH}$=7.6 Hz, 3H) ° MS (EI$^+$): m/z 524 (M)$^+$. The chemical structure of the white crystal is Preparation of ruthenium Complex Example 1

(4,4',4"-ethoxycarbonyl-terpyridine) RuCl$_3$ (100 mg, 0.15 mmol), the product of Synthesis Example 1 (54.4 mg, 0.15 mmol), and potassium acetate (74.7 mg, 0.76 mmol) were disposed in a 50 ml single neck bottle, followed by adding xylene (30 ml) and heating under reflux for 20 hours under a nitrogen gas atmosphere. After the reaction was finished, the mixture was cooled to room temperature, followed by reduced pressure distillation to remove solvent and column chromatography using a mixture of ethyl acetate and dichloromethane (ethyl acetate: dichloromethane=1:6) as an eluent. An eluate was collected followed by removing the eluent using a rotary evaporator. A brown solid product was obtained (115 mg, 83% yield).

The spectrum analysis for the brown solid product is: $^1$H NMR (400 MHz, d$_6$-acetone, 298K), δ(ppm): 9.40 (s, 2H), 9.00 (s, 2H), 8.26 (t, J$_{HH}$=5.6 Hz, 1H), 8.21~8.13 (m, 2H), 8.00 (s, 1H), 7.83 (d, J$_{HH}$=5.6 Hz, 2H), 7.61 (d, J$_{HH}$=5.6 Hz, 2H), 7.30 (s, 1H), 6.58 (dd, $J_{HH}$=7.6 Hz, 1.2 Hz, 1H), 5.44 (d, $J_{HH}$327.6 Hz, 1H), 4.35~3.80 (m, 6H), 1.40~0.80 (m, 9H).

The resultant brown solid product (82.0 mg, 0.090 mmol) was disposed in a 50 ml single neck bottle, followed by adding acetone (15 ml) and a sodium hydroxide solution (1 ml, 1M) and heating under reflux for 2 hours under a nitrogen gas atmosphere. After the reaction was finished, the mixture was cooled to room temperature, followed by solvent removal by means of reduced pressure distillation. Thereafter, water (5 ml) was added and a hydrogen chloride solution (2N) was added to adjust pH to about 3~4, followed by washing several times using deionized water, acetone and dichloromethane, and centrifuging so as to obtain a dark brown solid product (63.0 mg, 85% yield) (hereinafter referred to as ruthenium complex A-1).

The spectrum analysis for the ruthenium complex A-1 is: $^1$H NMR (400 MHz, $d_6$-dimethyl sulfoxide, 298K), δ(ppm): 9.28 (s, 2H), 9.14 (s, 2H), 8.36 (d, $J_{HH}$=7.2 Hz, 1H), 8.22~8.05 (m, 3H), 7.66 (d, $J_{HH}$=6.0 Hz, 2H), 7.61 (d, $J_{HH}$=6.0 Hz, 2H), 7.28 (s, 1H), 6.61 (d, $J_{HH}$=7.6 Hz, 1H), 5.52 (d, $J_{HH}$=7.6 Hz, 1H); $^{19}$F-{$^1$H} NMR (470 MHz, $d_6$-dimethyl sulfoxide, 298K), δ(ppm): −58.33 (s, 3F), −60.13 (s, 3F); MS (FAB, $^{102}$Ru): m/z 822 (M)$^+$. The element analysis data is: C: 48.73%; N: 9.59%; H: 2.78%.

The chemical structure of the ruthenium complex A-1 is

Example 2

(4,4',4''-ethoxycarbonyl-terpyridine) RuCl$_3$ (100 mg, 0.15 mmol), the product of Synthesis Example 2 (54.4 mg, 0.15 mmol), and potassium acetate (74.7 mg, 0.76 mmol) were disposed in a 50 ml single neck bottle, followed by adding xylene (25 ml) and heating under reflux for 14 hours under a nitrogen gas atmosphere. After the reaction was finished, the mixture was cooled to room temperature, followed by reduced pressure distillation to remove solvent and column chromatography using a mixture of ethyl acetate and dichloromethane (ethyl acetate: dichloromethane=1:4) as an eluent. An eluate was collected followed by removing the eluent using a rotary evaporator. A brown solid product was obtained (112 mg, 81% yield).

The spectrum analysis for the brown solid product is: $^1$H NMR (400 MHz, $d_6$-acetone, 298K), δ(ppm): 9.37 (s, 2H), 9.10 (s, 2H), 8.36 (dd, $J_{HH}$=6.4 Hz, 2.4 Hz, 1H), 8.30~8.22 (m, 2H), 8.02 (d, $J_{HH}$=8.4 Hz, 1H), 7.83 (d, $J_{HH}$=5.6 Hz, 2H), 7.67 (dd, $J_{HH}$=5.6 Hz, 1.2 Hz, 2H), 6.95 (d, $J_{HH}$=7.6 Hz, 1H), 5.72 (s, 1H), 4.45~4.21 (m, 6H), 1.40~1.20 (m, 9H).

The resultant brown solid product (85.0 mg, 0.094 mmol) was disposed in a 50 ml single neck bottle, followed by adding acetone (15 ml) and a sodium hydroxide solution (1 ml, 1M) and heating under reflux for 2 hours under a nitrogen gas atmosphere. After the reaction was finished, the mixture was cooled to room temperature, followed by removing solvent by means of reduced pressure distillation. Thereafter, water (5 ml) was added and a hydrogen chloride solution (2N) was added to adjust pH to about 3~4, followed by washing several time using deionized water, acetone and dichloromethane, and centrifuging to obtain a dark brown solid product (90.0 mg, 81% yield) (hereinafter referred to as ruthenium complex A-2).

The spectrum analysis for the ruthenium complex A-2 is: $^1$H NMR (400 MHz, $d_6$-dimethyl sulfoxide, 298K) δ(ppm): 9.40 (s, 2H), 9.16 (s, 2H), 8.42 (t, $J_{HH}$=4.8 Hz, 1H), 8.22 (d, $J_{HH}$=4.8 Hz, 2H), 8.06 (d, $J_{HH}$=8.4 Hz, 1H), 7.65 (d, $J_{HH}$=5.6 Hz, 2H), 7.61 (d, $J_{HH}$=5.6 Hz, 2H), 6.96 (d, $J_{HH}$=5.6 Hz, 1H), 5.60 (s, 1H); MS (FAB, $^{102}$Ru): m/z 823 (M)$^+$; $^{19}$F-{$^1$H} NMR (470 MHz, $d_6$-dimethyl sulfoxide, 298K), δ(ppm): −61.22 (s, 3F), −62.12 (s, 3F). The element analysis data is: C: 48.06%; N: 11.29%; H: 2.56%.

The chemical structure of the ruthenium complex A-2 is

Example 3

(4,4',4''-ethoxycarbonyl-terpyridine) RuCl$_3$ (100 mg, 0.15 mmol), the product of Synthesis Example 3 (54.4 mg, 0.15 mmol), and potassium acetate (74.7 mg, 0.76 mmol) were disposed in a 50 ml single neck bottle, followed by adding xylene (25 ml) and heating under reflux for 14 hours under a nitrogen gas atmosphere. After the reaction was finished, the mixture was cooled to room temperature, followed by reduced pressure distillation to remove solvent and column chromatography using a mixture of ethyl acetate and dichloromethane (ethyl acetate: dichloromethane=1:5) as an eluent. An eluate was collected followed by removing the eluent using a rotary evaporator. A brown solid product was obtained (94.4 mg 68% yield).

The spectrum analysis of the brown solid product is: $^1$H NMR (400 MHz, $d_6$-acetone, 298K), δ(ppm): 9.32 (s, 2H), 9.00 (s, 2H), 8.43 (dd, $J_{HH}$=7.6 Hz, 1.6 Hz, 1H), 8.32~8.22 (m, 2H), 8.06 (s, 1H), 7.82 (d, $J_{HH}$=5.6 Hz, 2H), 7.62 (d, $J_{HH}$=4.4 Hz, 2H), 6.62 (d, $J_{HH}$=8.0 Hz, 1H), 5.56 (d, $J_{HH}$=8.0 Hz, 1H), 4.38~4.00 (m, 6H), 1.32~1.02 (m, 9H).

The resultant brown solid product (87.0 mg, 0.096 mmol) was disposed in a 50 ml single neck bottle, followed by adding acetone (15 ml) and a sodium hydroxide solution (1 ml, 1M) and heating under reflux for 2 hours under a nitrogen gas atmosphere. After the reaction was finished, the mixture was cooled to room temperature, followed by solvent removal by means of reduced pressure distillation. Thereafter, water (5 ml) was added and a hydrogen chloride solution (2N) was added to adjust pH to about 3~4, followed by washing several times using deionized water, acetone and dichloromethane, and centrifuging so as to obtain a dark brown solid product (69.4 mg, 88% yield) (hereinafter referred to as ruthenium complex A-3).

The spectrum analysis for the ruthenium complex A-3 is: $^1$H NMR (400 MHz, d$_6$-dimethyl sulfoxide, 298K) δ(ppm): 9.38 (s, 2H), 9.14 (s, 2H), 8.51 (t, J$_{HH}$=4.8 Hz, 1H), 8.25~8.10 (m, 3H), 7.64 (d, J$_{HH}$=6.0 Hz, 2H), 7.61 (d, J$_{HH}$=6.0 Hz, 2H), 6.68 (d, J$_{HH}$=7.6 Hz, 1H), 5.59 (d, J$_{HH}$=7.6 Hz, 1H); MS (FAB, $^{102}$Ru): m/z 823 (M)$^+$; $^{19}$F-{$^1$H} NMR (470 MHz, d$_6$-dimethyl sulfoxide, 298K), δ(ppm): −60.21 (s, 3F), −62.11 (s, 3F). The element analysis data is: C: 48.14%; N: 11.25%; H: 2.48%.

The chemical structure of the ruthenium complex A-3 is

Example 4

(4,4',4''-ethoxycarbonyl-terpyridine) RuCl$_3$ (120 mg, 0.18 mmol), the product of Synthesis Example 4 (68.7 mg, 0.18 mmol), and potassium acetate (89.6 mg, 0.91 mmol) were disposed in a 50 ml single neck bottle, followed by adding xylene (30 ml) and heating under reflux for 12 hours under a nitrogen gas atmosphere. After the reaction was finished, the mixture was cooled to room temperature, followed by reduced pressure distillation to remove solvent and column chromatography using a mixture of ethyl acetate and dichloromethane (ethyl acetate: dichloromethane=1:5) as an eluent. An eluate was collected followed by removing the eluent using a rotary evaporator. A brown solid product was obtained (115 mg, 68% yield).

The spectrum analysis of the brown solid product is: $^1$H NMR (400 MHz, d$_6$-acetone, 298K), δ(ppm): 9.34 (s, 2H). 9.07 (s, 2H), 8.42~8.36 (m, 1H), 8.25 (d, J$_{HH}$=5.2 Hz, 2H), 8.10 (d, J$_{HF}$=6.8 Hz, 1H), 7.81 (d, J$_{HH}$=5.8 Hz, 2H), 7.67 (d, J$_{HH}$=5.6 Hz, 2H), 5.37 (d, J$_{HF}$=11.2 Hz, 1H), 4.40~4.20 (m, 6H), 1.35~1.25 (m, 9H).

The resultant brown solid product (101 mg, 0.11 mmol) was disposed in a 50 ml single neck bottle, followed by adding acetone (15 ml) and a sodium hydroxide solution (1 ml, 1M) and heating under reflux for 2 hours under a nitrogen gas atmosphere. After the reaction was finished, the mixture was cooled to room temperature, followed by solvent removal by means of reduced pressure distillation. Thereafter, water (5 ml) was added and a hydrogen chloride solution (2N) was added to adjust pH to about 3~4, followed by washing several times using deionized water, acetone and dichloromethane, and centrifuging so as to obtain a dark brown solid product (76.0 mg, 83% yield) (hereinafter referred to as ruthenium complex A-4).

The spectrum analysis for the ruthenium complex A-4 is: $^1$H NMR (400 MHz, d$_6$-dimethyl sulfoxide, 298K) δ(ppm): 9.37 (s, 2H), 9.13 (s, 2H), 8.49 (t, J$_{HH}$=4.6 Hz, 1H), 8.22~8.15 (m, 3H), 7.66 (d, J$_{HH}$=5.6 Hz, 2H), 7.58 (d, J$_{H}$H=6.0 Hz, 2H), 5.36 (d, J$_{HF}$=10.8 Hz, 1H); MS (FAB, $^{102}$Ru): m/z 842 (M+1)$^+$; $^{19}$F-{$^1$H} NMR (470 MHz, d$_6$-dimethyl sulfoxide, 298K), δ(ppm): −59.07 (s, 3F), −62.12 (s, 3F), −117.76 (s, 1F). The element analysis data is: C: 46.08%; N: 11.15%; H: 2.33%.

The chemical structure of the ruthenium complex A-4 is

Example 5

(4,4',4''-ethoxycarbonyl-terpyridine)RuCl$_3$ (120 mg, 0.18 mmol), the product of Synthesis Example 5 (95.8 mg, 0.18 mmol), and potassium acetate (89.6 mg, 0.91 mmol) were disposed in a 50 ml single neck bottle, followed by adding xylene (30 ml) and heating under reflux for 12 hours under a nitrogen gas atmosphere. After the reaction was finished, the mixture was cooled to room temperature, followed by reduced pressure distillation to remove solvent and column chromatography using a mixture of ethyl acetate and dichloromethane (ethyl acetate: dichloromethane=1:8) as an eluent. An eluate was collected followed by removing the eluent using a rotary evaporator. A brown solid product was obtained (113 mg, 58% yield).

The spectrum analysis for the brown solid product is: $^1$H NMR (400 MHz, CDCl$_3$, 298K), δ(ppm): 9.03 (s, 2H), 8.81 (s, 2H), 8.51 (s, 1H), 8.07 (s, 1H), 7.77 (d, J$_{HH}$=8.0 Hz, 1H), 7.68 (d, J$_{HH}$=3.6 Hz, 1H), 7.64 (d, J$_{HH}$=6.0 Hz, 2H), 7.59 (d, J$_{HH}$=6.0 Hz, 2H), 6.95 (d, J$_{HH}$=3.6 Hz, 1H), 6.91 (d, J$_{HH}$=8.0 Hz, 1H), 5.54 (s, 1H), 4.64 (q, J$_{HH}$=7.2 Hz, 2H), 4.40 (q, J$_{HH}$=7.2 Hz, 4H), 2.95 (t, J$_{HH}$=7.6 Hz, 2H), 1.78 (q, J$_{HH}$=7.6 Hz, 2H), 1.60 (t, J$_{HH}$=7.2 Hz, 3H), 1.50~1.30 (m, 12H), 0.92 (t, J$_{HH}$=6.8 Hz, 3H).

The resultant brown solid product (101 mg, 0.11 mmol) was disposed in a 50 ml single neck bottle, followed by adding acetone (15 ml) and a sodium hydroxide solution (1 ml, 1M) and heating under reflux for 2 hours under a nitrogen gas atmosphere. After the reaction was finished, the mixture was cooled to room temperature, followed by solvent removal by means of reduced pressure distillation. Thereafter, water (5 ml) was added and a hydrogen chloride solution (2N) was added to adjust pH to about 3~4, followed by washing several times using deionized water, acetone and dichloromethane, and centrifuging so as to obtain a dark brown solid product (94.0 mg, 83% yield) (hereinafter referred to as ruthenium complex A-5).

The spectrum analysis for the ruthenium complex A-5 is: $^1$H NMR (400 MHz, $d_6$-dimethyl sulfoxide, 298K) δ(ppm): 9.36 (s, 2H), 9.11 (s, 2H), 8.61 (s, 1H), 8.29 (s, 1H), 8.25 (d, $J_{HH}$=8.0 Hz, 1H), 8.15 (d, $J_{HH}$=3.6 Hz, 1H), 7.69 (d, $J_{HH}$=6.0 Hz, 2H), 7.62 (d, $J_{HH}$=6.0 Hz, 2H), 7.10 (d, $J_{HH}$=3.6 Hz, 1H), 6.97 (d, $J_{HH}$=8.0 Hz, 1H), 5.61 (s, 1H), 2.95 (t, $J_{HH}$=6.8 Hz, 2H), 1.74 (q, $J_{HH}$=6.8 Hz, 2H), 1.48~1.25 (m, 6H), 0.89 (t, $J_{HH}$=6.8 Hz, 3H); MS (FAB, $^{102}$Ru): m/z 989 (M)$^+$; $^{19}$F-{$^1$H} NMR (470 MHz, $d_6$-dimethyl sulfoxide, 298K), δ(ppm): −61.20 (s, 3F), −62.07 (s, 3F). The element analysis data is: C: 46.47%; N: 9.19%; H: 3.75%.

The chemical structure of the ruthenium complex A-5 is

Comparative Example

N749 dye was commercially available from Solaronix SA Co., Switzerland, model no.: Ruthenizer 620-1H3TBA. Before the following tests were conducted, the concentration of N749 dye was adjusted to 0.3 mM using absolute alcohol, followed by adding chenodeoxycholic acid (CDCA, 20nM).

[Tests]

1. Measurement of Molar Extinction Coefficient:

Each of the 2-phenyl-6-azolylpyridine-based ligands of Synthesis Examples 1~5, the ruthenium complexes of Examples 1~5 and N749 dye of Comparative Example was dissolved in DMF, followed by measuring molar extinction coefficients thereof using a UV-Visible Spectrophotometer (Hitachi Spectrophotometer; Model no.: U-3900).

2. Measurement of Redox Potential

Each of the ruthenium complexes of Examples 1~5 and N749 dye of Comparative Example was dissolved in dimethylformamide, followed by adding a TBAPF$_6$ solution (0.1M). The redox potential was measured by a cyclic voltammetry measurement using an electrochemical analyzer (CH Instruments; Model no.: Electrochemical Analyzer CHI621a), in which Fc/Fc$^+$ was used as an internal standard, Ag/AgNO$_3$ was used as a reference electrode, Pt was used as an auxiliary electrode, glassy carbon was used as a working electrode and a scanning speed was 20 mVs$^{-1}$. The obtained potential can be converted to NHE potential by adding 0.630V. The $E_{0-0}$ value was estimated from the intersection of absorption and emission spectra.

3. Measurement of Photoelectric Conversion Efficiency

It is noted that the manufacturing process of a dye-sensitized solar cell is well known in the art and the following examples are used for illustration, and should not be construed as limiting the implementation of the present invention.

To manufacture the dye-sensitized solar cell, a slurry containing titanium dioxide nanoparticles was printed on a conductive glass substrate, followed by sintering in a high temperature furnace to obtain a sintered substrate with a total thickness of 20 micrometers. Next, the sintered substrate was immersed in a titanium tetrachloride aqueous solution (40 mM) and was placed in an oven at 75° C. for 30 minutes, followed by rinsing with deionized water and ethanol to form a conductive substrate containing titanium dioxide. Six conductive substrates containing titanium dioxide were immersed respectively in solutions containing the ruthenium complexes of Examples 1~5 of the present invention and the N749 dye of Comparative Example at room temperature for 18 hours, followed by taking out from the solutions and washing with absolute alcohol to form six first electrodes.

A chloroplatinic acid solution in isopropanol (10 µl, 50 mM) was dropped onto each of six fluoride-doped tin oxide conductive glasses, followed by thermal cracking at 450° C. for 15 minutes for reduction to platinum metals. Six second electrodes were thus obtained.

The first and second electrodes were packaged in pairs using a hot melting polymer film, and an electrolytic component was injected into pre-drilled small holes in the second electrodes. Next, the small holes were sealed using the hot melting polymer film and small pieces of glasses, thereby obtaining six dye-sensitized solar cells. The electrolytic component is a TBAPF$_6$ solution (0.1M).

The dye-sensitized solar cells were irradiated by a solar simulator (150W xenon lamp; Class A, Newport Oriel; Model no.: 91159) that provides a simulation light with air mass (AM) 1.5 Global radiation and an intensity of 100 mW/cm$^2$. An external voltage was applied to each of the dye-sensitized solar cells using a digital electrometer (Keithley; Model no.: 2400), and the currents thereof were recorded. Data were collected to plot a graph of voltage vs. current density. In this graph of voltage vs. current density, $V_{OC}$ which is an open circuit voltage when current density is 0 and $J_{SC}$ which is a short circuit current value when a voltage is 0 were obtained to evaluate the photoelectric conversion efficiency. Specifically, the photoelectric conversion efficiency is obtained by dividing the maximum value of the product of the voltage and the current density by the incident light intensity.

4. Measurement of the Long-Term Stability of the Solar Cell

Dye-sensitized solar cells were prepared in a way similar to that described in the above section of "Measurement of photoelectric conversion efficiency", except that the electrolytic component was replaced by a mixture solution containing 1,3-dimethylimidazolium iodide (2M), lithium iodide (0.05M), iodine (0.03M), guanidinium thiocyanate (0.1M), and N-butyl-1H-benzimidazole (NBB, 0.5M) in 3-methyoxy propanenitrile.

Each of the dye-sensitized solar cells was covered with a polymer film that is capable of shielding ultraviolet light, and was placed in a lightfastness testing equipment (ATLAS GmbH; Model no.: Suntest CPS+). Thereafter, the dye-sensitized solar cells were radiated continuously using the solar simulator, and hot air was introduced into a closed environment where the dye-sensitized solar cells were placed, and the environment temperature was kept at 60° C. The dye-sensitized solar cells were taken out to measure the voltage and current every 100 hours until the total radiation time reached 1000 hours.

TABLE 1

| | Example | | | | | |
|---|---|---|---|---|---|---|
| | E1 | E2 | E3 | E4 | E5 | CE |
| $E_{ox}$ (V vs NHE) | 0.84 | 0.92 | 0.92 | 0.96 | 0.92 | 0.88 |
| $E_{0-0}$ (V vs NHE) | 1.57 | 1.69 | 1.64 | 1.79 | 1.70 | 1.66 |
| $E = E_{ox} - E_{0-0}$ (V) | −0.73 | −0.77 | −0.72 | −0.83 | −0.78 | −0.78 |
| $J_{SC}$ (mA·cm$^{-2}$) | 11.93 | 18.09 | 17.00 | 17.62 | 16.26 | 17.33 |
| $V_{OC}$ (V) | 0.63 | 0.71 | 0.70 | 0.75 | 0.71 | 0.72 |
| Fill factor (FF) | 0.633 | 0.682 | 0.687 | 0.684 | 0.679 | 0.701 |
| Photo-electric conversion efficiency (η, %) | 4.76 | 8.76 | 8.18 | 9.04 | 7.84 | 8.75 |

Figure 1:
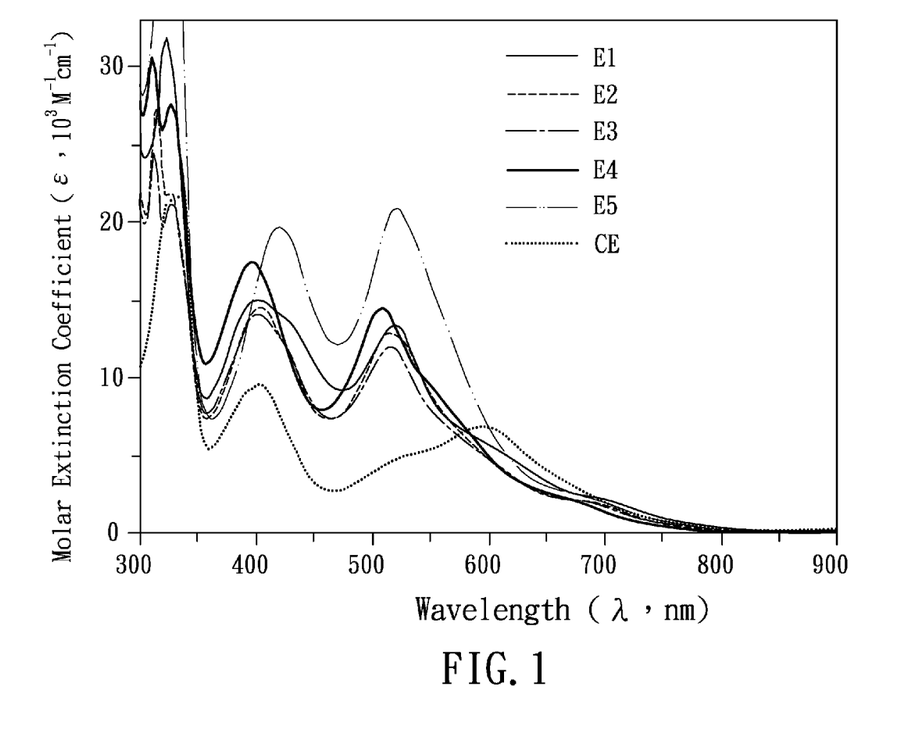
FIG. 1 is a graph illustrating the absorption spectrum of the ruthenium complexes of the preferred embodiments according to the present invention and the absorption spectrum of N749 dye of a comparative example.

From FIG. 1, it is revealed that the absorption of the ruthenium complexes of Examples 1~5 of the present invention in the near infrared region is comparable to that of the N749 dye of Comparative example, and the absorption in the visible light and the molar extinction coefficient are superior to those of the N749 dye.

In addition, from Table 1, the electrical property ($E_{OX}$ and $E_{0-0}$) of the ruthenium complexes of Examples 2~5 of the present invention are comparable to that of the N749 dye, the photoelectric conversion efficiency of the ruthenium complexes of Examples 2 and 3 of the present invention (8.76% and 8.18%) are comparable to that of the N749 dye (8.75%), and the photoelectric conversion efficiency of the ruthenium complex of Example 4 of the present invention (9.04%) is superior to that of the N749 dye (8.75%). The electrical property of the ruthenium complex of Example 1 is comparable to that of the N749 dye. Although the photoelectric conversion efficiency of the ruthenium complex of Example 1 (4.76%) is inferior to that of the N749 dye, since there is no NCS group in the ruthenium complex, the dye-sensitized solar cell composed of the ruthenium complex of the present invention would exhibit longer lifespan.

The $E_{OX}$ of the ruthenium complexes of Examples 2, 3, 4 and 5 are greater than 0.9V because there are three nitrogen atoms on the azolyl group. This indicates that the ruthenium complex of the present invention can match the energy level of the electrolytic component to achieve optimum regeneration efficiency.

Figure 2:
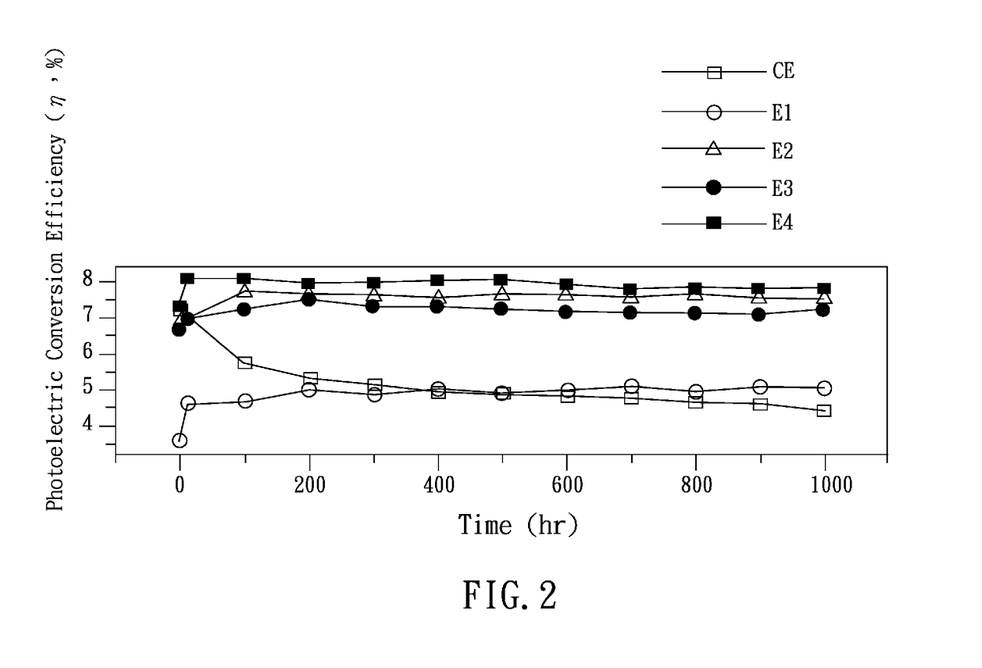
FIG. 2 is a graph illustrating the photoelectric conversion efficiency of the dye-sensitized solar cells to which the ruthenium complexes of the preferred embodiments according to the present invention and the comparative example are applied during a long period of use.

From FIG. 2, it is evident that after the 1000-hour test, the degradation percentage of the photoelectric conversion efficiency of the dye-sensitized solar cell having the N749 dye is 39% (reduced from 7.25% to 4.42%). The photoelectric conversion efficiency of the dye-sensitized solar cell having the ruthenium complex of Example 1 has no substantial degradation (maintained at about 5.05%). The degradation percentage in the photoelectric conversion efficiency of the dye-sensitized solar cell having the ruthenium complex of Example 2 is 2.7% (reduced from 7.71% to 7.5%). The degradation percentage in the photoelectric conversion efficiency of the dye-sensitized solar cell having the ruthenium complex of Example 3 is 5.7% (reduced from 7.49% to 7.06%). The degradation percentage in the photoelectric conversion efficiency of the dye-sensitized solar cell having the ruthenium complex of Example 4 is 3.9% (reduced from 8.07% to 7.76%). Therefore, when the ruthenium complex of the present invention is applied to the dye-sensitized solar cell, the dye-sensitized solar cell can have improved photoelectric conversion efficiency and lifespan. In addition, in the synthesis method of the present invention, the yield of the ruthenium complex of the present invention is greater than sixty percent. As compared to the conventional ruthenium complex employed in the dye-sensitized solar cell, the ruthenium complex of the present invention can be mass-produced and applied to the industry.

To sum up, by virtue of the structural design of 2-phenyl-6-azolylpyridine-based ligand, the ligand can have an improved absorption in the visible light region and near infrared light region, and the transition metal complex containing the 2-phenyl-6-azolylpyridine-based ligand has an absorption spectrum matching the solar spectrum. Therefore, the absorption of the transition metal complex in the visible light region and near infrared light region can be enhanced. In addition, when the transition metal complex is subsequently applied to a dye-sensitized solar cell, the dye-sensitized solar cell has improved photoelectric conversion efficiency and lifespan.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

What is claimed is:

1. A 2-phenyl-6-azolylpyridine-based ligand represented by the following formula (I):

(I)

wherein, X represents nitrogen or C—R$^{10}$; R$^2$, R$^3$, R$^4$, R$^5$, R$^6$, R$^7$, R$^8$ and R$^{10}$ independently represent hydrogen, halogen, a cyano group, an amino group, an optionally substituted aryl group, an optionally substituted heteroaryl group, sulfate, —COOH, an alkoxy group, a carbonyl group, a C$_1$-C$_{10}$ haloalkyl group, a C$_1$-C$_{12}$ alkyl group, a C$_2$-C$_{10}$ alkenyl group, a C$_2$-C$_{10}$ alkynyl group, a C$_3$-C$_{20}$ cycloalkyl group, a C$_3$-C$_{20}$ cycloalkenyl group, a C$_1$-C$_{20}$ heterocycloalkyl group, or a C$_1$-C$_{20}$ heterocycloalkenyl group; and R$^9$ represents hydrogen or alkali metal, wherein R$^1$ is CF$_3$.

2. The 2-phenyl-6-azolylpyridine-based ligand of claim 1, wherein X is C—R$^{10}$.

3. The 2-phenyl-6-azolylpyridine-based ligand of claim 1, wherein X is nitrogen.

4. The 2-phenyl-6-azolylpyridine-based ligand of claim 1, wherein at least one of R$^5$, R$^6$, R$^7$, and R$^8$ is F or CF$_3$.

5. The 2-phenyl-6-azolylpyridine-based ligand of claim 1, wherein the optionally substituted aryl group is wherein $R^{19}$ and $R^{20}$ independently represent hydrogen, halogen, a cyano group, an amino group, an aryl group, a heteroaryl group, an alkoxy group, a $C_1$-$C_{10}$ haloalkyl group, a $C_1$-$C_{12}$ alkyl group, a $C_2$-$C_{10}$ alkenyl group, a $C_2$-$C_{10}$ alkynyl group, a $C_3$-$C_{20}$ cycloalkyl group, a $C_3$-$C_{20}$ cycloalkenyl group, a $C_1$-$C_{20}$ heterocycloalkyl group, or a $C_1$-$C_{20}$ heterocycloalkenyl group.

6. The 2-phenyl-6-azolylpyridine-based ligand of claim 1, wherein the optionally substituted heteroaryl group is selected from the group consisting of wherein $R^{11}$, $R^{12}$, $R^{13}$, $R^{14}$, $R^{15}$, $R^{16}$, $R^{21}$ and $R^{22}$ independently represent hydrogen, halogen, a cyano group, an amino group, an aryl group, a heteroaryl group, an alkoxy group, a $C_1$-$C_{10}$ haloalkyl group, a $C_1$-$C_{12}$ alkyl group, a $C_2$-$C_{10}$ alkenyl group, a $C_2$-$C_{10}$ alkynyl group, a $C_3$-$C_{20}$ cycloalkyl group, a $C_3$-$C_{20}$ cycloalkenyl group, a $C_1$-$C_{20}$ heterocycloalkyl group, or a $C_1$-$C_{20}$ heterocycloalkenyl group.

7. The 2-phenyl-6-azolylpyridine-based ligand of claim 1, wherein the amino group is represented by —$NR^{17}R^{18}$, wherein $R^{17}$ and $R^{18}$ independently represent hydrogen, halogen, a cyano group, an amino group, an aryl group, a heteroaryl group, an alkoxy group, a $C_1$-$C_{10}$ haloalkyl group, a $C_1$-$C_{12}$ alkyl group, a $C_2$-$C_{10}$ alkenyl group, a $C_2$-$C_{10}$ alkynyl group, a $C_3$-$C_{20}$ cycloalkyl group, a $C_3$-$C_{20}$ cycloalkenyl group, a $C_1$-$C_{20}$ heterocycloalkyl group, or a $C_1$-$C_{20}$ heterocycloalkenyl group.

8. The 2-phenyl-6-azolylpyridine-based ligand of claim 1, wherein alkoxy is —$OR^{23}$, $R^{23}$ representing aryl, heteroaryl, $C_1$-$C_{10}$ haloalkyl, $C_1$-$C_{12}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, or $C_1$-$C_{20}$ heterocycloalkenyl.

9. The 2-phenyl-6-azolylpyridine-based ligand of claim 1, wherein $R^3$ represents hydrogen, an aryl group, a heteroaryl group, an amino group, a $C_1$-$C_{12}$ alkoxy group, or wherein $R^{24}$ represents hydrogen, halogen, a cyano group, an amino group, an aryl group, a heteroaryl group, an alkoxy group, a $C_1$-$C_{10}$ haloalkyl group, a $C_1$-$C_{12}$ alkyl group, a $C_2$-$C_{10}$ alkenyl group, a $C_2$-$C_{10}$ alkynyl group, a $C_3$-$C_{20}$ cycloalkyl group, a $C_3$-$C_{20}$ cycloalkenyl group, a $C_1$-$C_{20}$ heterocycloalkyl group, or a $C_1$-$C_{20}$ heterocycloalkenyl group.

10. A transition metal complex represented by the following formula (II)

$$ML^1L^2 \qquad (II)$$

wherein M is a transition metal, $L^1$ is a 2-phenyl-6-azolylpyridine-based ligand, $L^2$ is a carboxy-bipyridine-based;

wherein said 2-phenyl-6-azolylpyridine-based ligand is represented by the following formula (I):

wherein, X represents nitrogen or C—$R^{10}$; $R^1$, $R^2$, $R^3$, $R^4$, $R^5$, $R^6$, $R^7$, $R^8$ and $R^{10}$ independently represent hydrogen, halogen, a cyano group, an amino group, an optionally substituted aryl group, an optionally substituted heteroaryl group, sulfate, —COOH, an alkoxy group, a carbonyl group, a $C_1$-$C_{10}$ haloalkyl group, a $C_1$-$C_{12}$ alkyl group, a $C_2$-$C_{10}$ alkenyl group, a $C_2$-$C_{10}$ alkynyl group, a $C_3$-$C_{10}$ cycloalkyl group, a $C_3$-$C_{20}$ cycloalkenyl group, a $C_1$-$C_{20}$ heterocycloalkyl group, or a $C_1$-$C_{20}$ heterocycloalkenyl group; and $R^9$ represents hydrogen or alkali metal.

11. The transition metal complex as claimed in claim 10, wherein M is a Group VIII transition metal.

12. The transition metal complex as claimed in claim 11, wherein M is ruthenium.

13. The transition metal complex as claimed in claim 11, wherein M is osmium.

14. The transition metal complex as claimed in claim 10, wherein the carboxy-bipyridine-based ligand is represented by the following formula (III):

(III)

wherein $X^1$, $X^2$, $X^3$, $X^4$, $X^5$, $X^6$, and $X^7$ independently represent hydrogen, halogen, $CF_3$, a $C_1$-$C_{12}$ linear alkyl group, a $C_1$-$C_{12}$ branched alkyl group, a phosphoryl group, a phosphate group, a boric acid group, a borate group, a sulfo group, a sulfonate group, or —COOY, Y being hydrogen, alkali metal, a $C_1$-$C_{12}$ linear alkyl group, a $C_1$-$C_{12}$ branched alkyl group or $N(C_4H_9)_4^+$; with the proviso that at least one of $X^1$, $X^2$, $X^3$, $X^4$, $X^5$, $X^6$, and $X^7$ is —COOY, $X^8$ is $X^9$, $X^{10}$, $X^{11}$, and $X^{12}$ independently represent hydrogen, halogen, $CF_3$, a carboxylic group, a $C_1$-$C_8$ linear alkyl group, a $C_1$-$C_8$ branched alkyl group, $X^{13}$ and $X^{14}$ independently represent hydrogen, halogen, $CF_3$, a carboxylic group, a $C_1$-$C_8$ linear alkyl group, a $C_1$-$C_8$ branched alkyl group, or $X^{15}$ and $X^{16}$ independently represent a $C_1$-$C_8$ linear alkyl group, a $C_1$-$C_8$ branched alkyl group, an alkoxy group, or an alkylthio group.

15. The transition metal complex as claimed in claim 14, wherein at least two of $X^1$, $X^2$, $X^3$, $X^4$, $X^5$, $X^6$, and $X^7$ are —COOY.

16. The transition metal complex as claimed in claim 15, wherein at least two of $X^1$, $X^2$, $X^3$, $X^4$, $X^5$, $X^6$, and $X^7$ are —COOH.

* * * * *